United States Patent [19]

Duranton

[11] Patent Number: 5,928,654
[45] Date of Patent: Jul. 27, 1999

[54] MODULATING BODY/CRANIAL HAIR GROWTH WITH LIPOXYGENASE/ CYCLOOXYGENASE INHIBITORS

[75] Inventor: Albert Duranton, Paris, France

[73] Assignee: Societe L'Oreal S.A., Paris, France

[21] Appl. No.: 08/834,162

[22] Filed: Apr. 14, 1997

[30] Foreign Application Priority Data

Apr. 17, 1996 [FR] France .................................. 96-04795

[51] Int. Cl.$^6$ ....................................................... A61K 7/00
[52] U.S. Cl. ......................... 424/401; 424/70.1; 424/465; 514/880
[58] Field of Search ..................... 424/400, 401, 424/70.1, 78.02; 514/827, 828, 880, 881, 946, 947; 220/500; 206/823, 465

[56] References Cited

U.S. PATENT DOCUMENTS

| | | | |
|---|---|---|---|
| 4,708,964 | 11/1987 | Allen | 514/533 |
| 4,722,837 | 2/1988 | Cameron | 424/70 |
| 4,849,445 | 7/1989 | Schaub | 514/443 |
| 4,944,939 | 7/1990 | Moore | 424/73 |
| 5,030,642 | 7/1991 | Fuller et al. | 514/357 |
| 5,075,330 | 12/1991 | Belliotti et al. | 514/450 |
| 5,220,025 | 6/1993 | Belliotti et al. | 544/298 |
| 5,641,755 | 6/1997 | Weichselbaum | 514/44 |
| 5,654,293 | 8/1997 | Francois et al. | 514/171 |

FOREIGN PATENT DOCUMENTS

| | | |
|---|---|---|
| 0321950 | 6/1989 | European Pat. Off. . |
| 0648488 | 4/1995 | European Pat. Off. . |
| 3409415 | 9/1985 | Germany . |
| WO 94/27563 | 12/1994 | WIPO . |
| WO 94/27586 | 12/1994 | WIPO . |
| WO 96/09806 | 4/1996 | WIPO . |

OTHER PUBLICATIONS

Baumann et al, Falvonoids and related compounds as inhibitors of arachidonic acid peroxidation, Prostaglandins, vol. 20, No. 4, pp. 627–639, Nov. 1980.

Chemical Abstracts, vol. 115, No. 20, Nov. 18, 1991, Columbus, Ohio, USA, Abstract No. 214519, C. Watanabe: "Hair tonics containing hormones and ginkgo extracts," XP002024235 & JP 03 161 426 A (Kobayashi Kose Co., Ltd.) Jul. 11, 1991.

Chemical Abstracts, vol. 112, No. 22, May 28, 1990, Columbus, Ohio, USA, Abstract No. 204493, Y. Tomita: "Skin-–lightening cosmetics containing antihistaminics, mas cell degranulation inhibitors, cyclooxygenase inhibitors, or lipoxygenase inhibitors." XP002024236 & JP 02 017 115 A (Shiseido Co., Ltd.) Jan. 22, 1990.

*Primary Examiner*—Thurman N. Page
*Assistant Examiner*—Lakshmi Channavajjala
*Attorney, Agent, or Firm*—Burns, Doane, Swecker & Mathis, L.L.P.

[57] ABSTRACT

The loss of body/cranial hair is promoted and/or its growth is slowed/prevented by topically and/or systemically administering to an individual in need of such treatment respectively effective amounts at least one lipoxygenase inhibitor and at least one cyclooxygenase inhibitor, or alternatively, an effective amount of an active agent that is both a lipoxygenase inhibitor and a cyclooxygenase inhibitor.

21 Claims, No Drawings

MODULATING BODY/CRANIAL HAIR GROWTH WITH LIPOXYGENASE/ CYCLOOXYGENASE INHIBITORS

CROSS-REFERENCE TO COMPANION APPLICATION

Copending application Ser. No. 08/322,198, filed Oct. 13, 1994, and assigned to the assignee hereof.

BACKGROUND OF THE INVENTION

1. Technical Field of the Invention

The present invention relates to novel cosmetic and/or therapeutic compositions for modifying the growth of body hair and/or of head (cranial) hair, comprising at least one lipoxygenase inhibitor and at least one cyclooxygenase inhibitor.

The present invention more especially relates to novel cosmetic and/or therapeutic compositions that either promote the loss of body hair and/or of head hair, or reduce/ retard or prevent the growth thereof, which comprise at least one lipoxygenase inhibitor and at least one cyclooxygenase inhibitor.

2. Description of the Prior Art

It is known to this art that certain polyunsaturated fatty acids, in particular those having 20 carbon atoms, such as arachidonic acid, dihomogammalinolenic acid or alternatively eicosapentaenoic acid, can be converted in vivo by the action of certain specific enzymes contained in living cells, in particular epithelial cells, to certain other eicosanoid-type compounds useful to the human body.

Thus, it is known to this art that the enzymes designated cyclooxygenases generate, from the various fatty acids indicated above, prostaglandin-type and thromboxane eicosanoids, and that the enzymes designated lipoxygenases are, for their part, responsible for the formation of leukotriene-type eicosanoids and other hydroxylated acyclic acids containing 20 carbon atoms. The same given polyunsaturated fatty acid (or substrate) will be able to initiate, according to the nature of the enzyme with which it will have first reacted, the formation of several different metabolites, namely, prostaglandins and leukotrienes, for example.

Polyunsaturated fatty acids, especially those which are $C_{20}$ (reactive raw materials), which are destined to be metabolized by the specific action of the cyclooxygenase and lipoxygenase enzymes, are generally provided in the body through certain foods, in particular certain natural oils of animal or plant origin. It is thus possible for this supply to be provided either in direct form (such is the case, for example, for arachidonic acid, which is present as such in egg whites), or indirectly in the form of precursor compounds (compounds which are also deemed "essential fatty acids," which are themselves unsaturated fatty acids, generally $C_{18}$–$C_{22}$, such as linoleic, α-linolenic and γ-linolenic acids) which will be converted by means of human metabolism, according to complex mechanisms which will not be repeated in detail herein, to suitable (namely, metabolizable) substrates for cyclooxygenases and lipoxygenases.

It too is known that the enzymatic conversions described above and the different reaction products which result therefrom exert a substantial influence on the mechanisms of body hair and/or cranial hair growth.

In this regard, the assignee hereof has demonstrated that by promoting either of these two enzymatic pathways, cyclooxygenases or lipoxygenases, in the cells of the skin and/or of the scalp, the growth of the body hair and/or of cranial hair could be modified substantially. This is described in EP-94/402055.

Essentially, this patent application describes promoting one of the pathways relative to the other by the administration of a combination of compounds associating an inhibitor of one of the pathways with a stimulator of the other pathway.

WO-94/27563 and WO-94/27586 describe reducing or even inhibiting the growth of body hair or of head hair by the administration of an effective amount either of a lipoxygenase inhibitor or of a cyclooxygenase inhibitor. The amounts of inhibitors which are recommended range from 1% to 30% by weight, or even more. Experience has shown that the desirable effects begin to be measurable from 5% and are only of practical interest at doses greater than 10% or 15%, if not 20%.

Without detracting from the merits of the above findings, it should be stressed that the compounds generally used may have side effects and may sometimes be toxic above certain doses. The consequence of this is that their application is difficult or even impossible, in particular for cosmetic applications.

Thus, need continues to exist for enhancing the efficacy of lipoxygenase and cyclooxygenase inhibitors, in particular to prevent their use at doses which are quite considerably less than the doses at which the undesirable side effects could appear.

SUMMARY OF THE INVENTION

It has now surprisingly and unexpectedly been found that the conjoint use of a lipoxygenase inhibitor and of a cyclooxygenase inhibitor presents the ability to inhibit the growth of body hair and/or head hair, and particularly at doses of each of the inhibitors at which, when these are taken individually do not exhibit any activity or, to the contrary, exhibit an opposite activity.

Herein, by lipoxygenase or cyclooxygenase "inhibitor" is intended any active agent or species which makes it possible, in vivo, to totally limit or inhibit the enzymatic activity of the lipoxygenases or of the cyclooxygenases, respectively.

By "topical route" is intended any technique for administration of a product by direct application thereof over a superficial (or external) part of the body, such as the skin, hair and the like, By "systemic route" is intended any technique for administration of a product by a route other than the topical route, for example the oral and/or parenteral routes.

Briefly, the present invention features cosmetic/ therapeutic compositions for promoting the loss of body hair and/or of head hair or for slowing down (retarding) and/or preventing the growth thereof, comprising at least one lipoxygenase inhibitor and at least one cyclooxygenase inhibitor.

This invention also features the use of at least one compound which is both a lipoxygenase inhibitor and a cyclooxygenase inhibitor.

In another embodiment of the present invention, featured are multicompartment packages or "kits", comprising, in a first compartment, one or more lipoxygenase inhibitors and, in a separate second compartment, one or more cyclooxygenase inhibitors, the compositions contained in said first and second compartments being here considered as combination compositions for simultaneous or separate use, or for a use extended over time, more particularly intended to modify the growth of body hair and/or of head hair.

DETAILED DESCRIPTION OF BEST MODE AND SPECIFIC/PREFERRED EMBODIMENTS OF THE INVENTION

More particularly according to the present invention, the inhibitory characteristics of a given active agent vis-à-vis lipoxygenases or cyclooxygenases may be conventionally determined by one skilled in this art especially by means of customary biochemical tests, generally based on chromatographic analytical techniques. Thus, these activities may, for example, be determined via the following techniques (non-limiting list) or with any other standard technique:

(1) activities in respect of 5, 12 and 15 lipoxygenases: exemplary is the technique entailing use of a biological material (human polynuclears, hair) incubated in the presence of C14 arachidonic acid or C14 linoleic acid; the hydroxy acids formed are extracted, separated by thin-layer chromatography or HPLC chromatography (Vanderhoeck J. Y. and Bailey J. M. in *J. Biol. Chem.*, 259, pp. 6752–6761 (1984); Huang M. et al., in *Cancer Res.*, 51, pp. 813–819 (1991); Baer A. N. and Green F. A. in *J. Lipids Res.*, 34, pp. 1505–1514 (1993); Ziboh V. A. et al., in *J. invest. Dermatol.*, 83, pp. 248–251 (1984)), (2) activities in respect of 5 lipoxygenase: exemplary are the spectrophotometric techniques described by Aharony D. and Stein R. L. in *J. Biol. Chem.*, 261, pp. 11512–11517 (1986), and by McMillan R. M. et al., in *Biochim. Biophys. Acta*, 1005, pp. 170–176 (1989), (3) activities in respect of cyclooxygenases: exemplary is the technique based on the use of a biological material (epidermis) incubated in the presence of C14 arachidonic acid; the hydroxy acids formed are extracted, separated by HPLC chromatography (Huang M. et al., in *Cancer Res.*, 51, pp. 813–819 (1991)) or identified by radioimmunoassays (Lysz T. W. and Needleman P. J. in *Neurochim.*, 38, pp. 1111–1117 (1982)). Also representative is the test described in the article "Nitric Oxide Activates Cyclooxygenase Enzymes," by D. Salvameni et al., *Proc. Natl. Sci. USA*, Vol. 90, pp. 7240–7244, Aug. 1993.

The lipoxygenase inhibitors are advantageously selected from among redox and non-redox inhibitors, precursors of redox inhibitors, antioxidants, iron chelating agents, imidazole-containing compounds, phenothiazines, benzopyran derivatives, as well as from among certain eicosanoids.

The redox inhibitor may be selected from among the derivatives of the catechol butanes (U.S. Pat. Nos. 5,008, 294, 4,708,964 and 4,880,637), such as nordihydroguaiaretic acid (NDGA), or one of the enantiomers thereof, such as masoprocol.

The redox inhibitor may also be selected from among phenidone, Ionapalen, indazolinones, naphazatrom, benzofuranol, alkylhydroxylamine, the compounds of the following formulae:

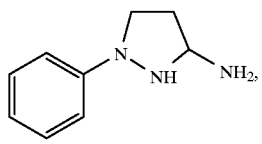

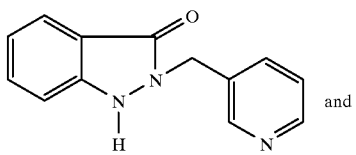

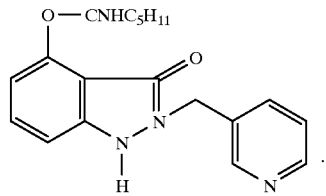

The non-redox inhibitors may be selected from among hydroxythiazoles, methoxyalkylthiazoles, benzopyrans and derivatives thereof, methoxytetrahydropyran, boswellic acids and acetylated derivatives thereof, quinolinemethoxyphenylacetic acids substituted with cycloalkyl radicals.

The antioxidant may be selected from among phenols, propyl gallate, flavonoids and naturally occurring compounds containing such flavonoids (Gingko biloba).

Exemplary flavonoids according to the invention include the hydroxylated derivatives of the flavones, such as flavonol, dihydroquercetin, luteolin, galangin, orobol. The derivatives of chalcone are also exemplary, such as 4,2',4'-trihydroxychalcone, ortho-aminophenols, N-hydroxyureas, benzofuranols, ebselen and agents capable of increasing the activity of reducing selenoenzymes.

The iron chelating agent is advantageously selected from among hydroxamic acids and derivatives thereof, N-hydroxyureas, 2-benzyl-1-naphthol, catechols, hydroxylamines, carnosol trolox C, catechol, naphthol, sulphasalazine, zyleuton, 5-hydroxyanthranilic acid and 4-(omega-arylalkyl)phenylalkanoic acids.

Exemplary imidazole-containing compounds include ketoconazole, itraconazole.

Exemplary eicosanoids inhibiting lipoxygenase include octadecatetraenoic, eicosatetraenoic, docosapentaenoic, eicosahexaenoic and docosahexaenoic acids, and their various esters, as well as various other eicosanoids, optionally in the form of esters, such as PGE1 (prostaglandin E1), PGA2 (prostaglandin A2), viprostol, 15-monohydroxyeicosatetraenoic, 15-monohydroxyeicosatrienoic and 15-monohydroxyeicosapentaenoic acids, leukotrienes B5, C5 and D5.

Various other compounds capable of inhibiting lipoxygenases include species which interfere with the calcium flows, in particular phenothiazines and diphenylbutylamines, verapamil, fuscoside, curcumin, chlorogenic acid, caffeic acid, 5,8,11,14-eicosatetrayenoic acid (ETYA), hydroxyphenylretinamide, Ionapalen, esculin, diethylcarbamazine, phenantroline, baicalein, proxicromil, thioethers and in particular diallyl sulfide and di-(1-propenyl) sulfide.

The cyclooxygenase inhibitors are advantageously nonsteroidal anti-inflammatory agents such as arylcarboxylic derivatives, pyrazole-containing derivatives, oxicam derivatives, nicotinic acid derivatives. Exemplary cyclooxygenase inhibitors also include meclofenamic acid (5659, Merck index, 11th edition), mefenamic acid (5680, Merck index, 11th edition), carprofen (1870, Merck index, 11th edition), diclofenac (3071, Merck index, 11th edition), diflunisal (3130, Merck index, 11th edition), fenbufen (3906, Merck index, 11th edition), fenoprofen (3926, Merck index, 11th edition), ibuprofen (4812, Merck index, 11th edition), indomethacin (4874, Merck index, 11th edition), ketoprofen (5184, Merck index, 11th edition), nabumetone (6258, Merck index, 11th edition), naproxen (6337, Merck index, 11th edition), sulindac (8961, Merck index, 11th edition), tenoxicam (9080, Merck index, 11th edition), tolmetin (9441, Merck index, 11th edition), or acetylsalicylic acid.

Lastly, exemplary compounds which may be used both as lipoxygenase inhibitor and cyclooxygenase inhibitor include, in particular, the corticoids such as dexamethasone or hydrocortisone, the fenamates such as morniflumate, the chalcone derivatives such as 3,4-dihydroxychalcone, or phospholipase $A_2$ inhibitors.

In general, according to the present invention it is of course envisaged to use mixtures of inhibitors, as long as these mixtures remain compatible with the desired effect.

According to the invention, the lipoxygenase inhibitor is advantageously employed in an amount ranging from 0.01% to 5% by weight, preferably ranging from 0.1% to 1% and even more preferably ranging from 0.1% to 0.8%.

Similarly, the cyclooxygenase inhibitor is advantageously employed in an amount ranging from 0.001% to 5% by weight and preferably ranging from 0.01% to 0.1%.

The compositions according to the invention are useful medicaments more particularly intended to promote the loss of body hair and/or of head hair or to retard or slow down and/or prevent the growth of body hair and/or of head hair.

In general, it will be appreciated that all of the above formulations may be conventionally packaged in a form suitable for the mode of administration or application intended for these products (lotions, shampoos, tablets, syrups and the like).

The compositions or "kits" according to the present invention are more particularly the following:

(a) the compositions comprising at least one lipoxygenase inhibitor and at least one cyclooxygenase inhibitor;

(b) the "kits" comprising, in a first compartment, at least one lipoxygenase inhibitor and, in a second separate compartment, at least one cyclooxygenase inhibitor.

As indicated above, each of the compositions as well as each of the components in the compartments of the kits are conventionally packaged in a form suitable for the various modes of administration or application envisaged for these components (lotions, shampoos, tablets, syrups and the like). Thus, the compositions and the kits are preferably packaged in a form suitable for topical application.

In general, per the present invention it is possible to design presentation kits containing as many separate compartments as inhibitors which it is desired or which it is advisable to use.

The compositions according to the invention, or the kits according to the invention, may also comprise various conventional and customary additives and adjuvants, in particular cosmetics additives in the case of topical applications (especially hair products), selected for example from among UV screening agents, thickening agents, penetrating agents such as urea, organic solvents such as ethanol, isopropanol, alkylene glycols, surfactants selected from among nonionic surfactants such as alkylpolyglycosides, cationic surfactants, anionic surfactants and amphoteric surfactants, colorants, antidandruff agents, perfumes and preservatives.

The present invention thus features a nontherapeutic treatment or regimen for modifying the growth of body hair and/or of head hair, comprising administering to the body, via the topical and/or systemic route, at least one lipoxygenase inhibitor and at least one cyclooxygenase inhibitor.

As indicated above, said administration may be made in combination simultaneously, separately or spaced out over time.

Preferably, these inhibitors are administered via the topical route.

In a particularly preferred embodiment for carrying out the regimen according to the invention, compositions containing immixture of the lipoxygenase and cyclooxygenase inhibitors are topically applied to the skin and/or the scalp.

To elicit beneficial effects, the rate of administration or of application of the compositions according to the invention is on the order of once to twice a day. In this regard, it has been noted that the sufficient effective amounts of inhibitory agents used are generally quite low.

The present invention is particularly useful for the treatment of various pathologies or afflicting the skin and/or the scalp, in particular hirsutism.

In order to further illustrate the present invention and the advantages thereof, the following specific examples are given, it being understood that same are intended only as illustrative and in nowise limitative.

EXAMPLE 1

Measurement of the Effect of the Combination of a Lipoxygenase Inhibitor and a Cyclooxygenase Inhibitor on the Regrowth of Body Hair In this experiment mice were used whose hair was in the inactive phase. A shaving will induce regrowth of the hair.

The animals were treated in lots corresponding to the different conditions to be tested.

For each lot, the regrowth time and the number of animals affected by this regrowth were measured.

The C57BL6 mouse was selected because in this animal, the synthesis of melanin occurs only in the active phase of regrowth. When the animals are shaved, they appear to have a pink skin. Only animals whose skin appeared completely pink after shaving were used in the experiment.

The animals were observed daily. The time required for the hair to appear was noted on the control lot (without treatment). An average regrowth time was thus determined. The number of animals in the test lots having an equivalent regrowth was then determined for the same time.

Inhibition of the regrowth of body hair was considered to exist when the average time was increased or when, for the same time, the number of animals having an equivalent regrowth Was reduced.

The animals were treated daily by the topical route at the dose of 50 μl of composition to be tested over 3 $cm^2$ for 35 days.

The control lot received only one composition consisting of the vehicle (propylene glycol 22.8%, ethanol 55.1% and water qs 100% (by weight)).

Lot A: control;

Lot B: indomethacin at 0.05 g/100 ml;

Lot C: NDGA at 1 g/100 ml;

Lot D: indomethacin at 0.05 g/100 ml+NDGA at 1 g/100 ml.

In the experiment, the average time was determined at 20 days.

|  | Lot A | Lot B | Lot C | Lot D |
|---|---|---|---|---|
| % of hairy animals at 20 days | 55 | 45 | 87 | 10 |

A chi-square test relating to the number of animals gave a degree of freedom of 3.00, a chi-square of 21.03 with a probability of 0.0001, indicating that under the experimental conditions, the combinatory immixture of the two inhibitors significantly prevented the regrowth of the hair.

EXAMPLE 2

In this example, various specific formulations according to the invention are set forth.

Composition 1: Leave-in lotion:

| NDGA | 0.10 g |
|---|---|
| Indomethacin | 0.05 g |
| Propylene glycol | 22.80 g |
| Ethanol 95% | 55.10 g |
| Purified water | qs 100.00 g |

Composition 2: Leave-in lotion:

| NDGA | 0.10 g |
|---|---|
| Ibuprofen | 0.25 g |
| Propylene glycol | 22.80 g |
| Ethanol 95% | 55.10 g |
| Purified water | qs 100.00 g |

Composition 3: Rinse-off lotion

| NDGA | 5.00 g |
|---|---|
| Indomethacin | 0.25 g |
| Propylene glycol | 22.80 g |
| Ethanol 95% | 55.10 g |
| Purified water | qs 100.00 g |

Composition 4: Leave-in lotion

| NDGA | 3.00 g |
|---|---|
| Meclofenamic acid | 0.25 g |
| Propylene glycol | 22.80 g |
| Ethanol 95% | 55.10 g |
| Purified water | qs 100.00 g |

Composition 5: Shampoo

| NDGA | 1.00 g |
|---|---|
| Tenoxicam | 0.25 g |
| Surfactant APG 300 | 15.00 g |
|  | AS (=30 g) |
| Purified water | qs 100.00 g |

Composition 6: Leave-in lotion

| Gingko biloba[1] | 5.00 g |
|---|---|
| Indomethacin | 0.25 g |
| Propylene glycol | 22.80 g |
| Ethanol 95% | 55.10 g |
| Purified water | qs 100.00 g |

[1] natural extract rich in flavonoids

Composition 7: Leave-in lotion

| Ketoconazole | 0.50 g |
|---|---|
| Indomethacin | 0.25 g |
| Propylene glycol | 22.80 g |
| Ethanol 95% | 55.10 g |
| Purified water | qs 100.00 g |

Composition 8: Leave-in lotion

| Diallyl sulfide | 5.00 g |
|---|---|
| Indomethacin | 0.25 g |
| Propylene glycol | 22.80 g |
| Ethanol 95% | 55.10 g |
| Purified water | qs 100.00 g | composition 9: Leave-in lotion

| Gingko biloba | 5.00 g |
|---|---|
| Indomethacin | 0.25 g |
| Linoleic acid | 5.00 g |
| Propylene glycol | 22.80 g |
| Ethanol 95% | 55.10 g |
| Purified water | qs 100.00 g |

Composition 10: Leave-in lotion

| Ketoconazole | 0.50 g |
|---|---|
| Ketoprofen | 0.20 g |
| Propylene glycol | 22.80 g |
| Ethanol 95% | 55.10 g |
| Purified water | qs 100.00 g |

Composition 11: Leave-in lotion

| Ketoconazole | 0.50 g |
|---|---|
| Acetylsalicylic acid | 0.25 g |
| Propylene glycol | 22.80 g |
| Ethanol 95% | 55.10 g |
| Purified water | qs 100.00 g |

Composition 12: Leave-in lotion

| Ionapalen | 1.00 g |
|---|---|
| Indomethacin | 0.25 g |
| Propylene glycol | 22.80 g |
| Ethanol 95% | 55.10 g |
| Purified water | qs 100.00 g |

Each of the compositions 1 to 12 provided good results in slowing down the growth of body hair and head hair.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for promoting the loss of body or cranial hair, or for slowing or preventing the growth thereof, comprising topically or systemically applying an effective amount of at least one lipoxygenase inhibitor and at least one cyclooxygenase inhibitor, or an effective amount of an active agent that functions both as a lipoxygenase inhibitor and a cyclooxygenase inhibitor.

2. The method as defined by claim 1, wherein said at least one lipoxygenase inhibitor is selected from the group consisting of redox and non-redox inhibitors, precursors of redox inhibitors, antioxidants, iron chelating agents, imidazole-containing compounds, phenothiazines, benzopyran derivatives, inhibitor eicosanoids, compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, Ionapalen, esculin, diethylcarbamazine, phenantroline, baicalein, proxicromil, thioethers, diallyl sulfide and di-(1-propenyl) sulfide.

3. The method as defined by claim 2, wherein said at least one redox inhibitor is a catechol butane derivative.

4. The method as defined by claim 3, wherein nordihydroguaiaretic acid (NDGA) or masoprocol is said redox inhibitor.

5. The method as defined by claim 2, wherein said at least one redox inhibitor is selected from the group consisting of phenidone, Ianopalen, indazolinones, naphazatrom, benzofuranol, alkylhydroxylamine, and the compounds of the following formulae:

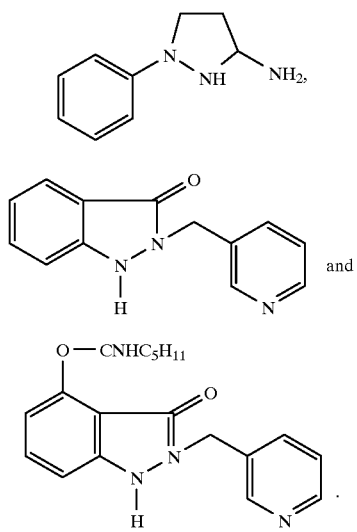

6. The method as defined by claim 2, wherein said at least one non-redox inhibitor is selected from the group consisting of hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals.

7. The method as defined by claim 2 wherein said at least one antioxidant is selected from the group consisting of phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes.

8. The method as defined by claim 2, said at least iron chelating agent selected from the group consisting of hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl) phenylalkanoic acids.

9. The method as defined by claim 2, said at least one imidazole-containing compound selected from the group consisting of ketoconazole and itraconazole.

10. The method as defined by claim 2, said at least one inhibitor eicosanoid selected from the group consisting of octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5.

11. The method as defined by claim 1, said at least one cyclooxygenase inhibitor selected from the group consisting of nonsteroidal anti-inflammatory agents.

12. The method as defined by claim 11, said at least one nonsteroidal anti-inflammatory agent selected from the group consisting of arylcarboxylic derivatives, pyrazole-containing derivatives, oxicam derivatives and nicotinic acid derivatives.

13. The method as defined by claim 11, wherein said at least one cyclooxygenase inhibitor is selected from the group consisting of meclofenamic acid, mefenamic acid, carprofen, diclofenac, diflunisal, fenbufen, fenoprofen, ibuprofen, indomethacin, ketoprofen, nabumetone, naproxen, sulindac, tenoxicam, tolmetin, and acetylsalicylic acid.

14. The method as defined by claim 1, wherein said inhibitors are topically administered.

15. The method as defined by claim 1, wherein said inibitors are systemically administered.

16. The method as defined by claim 1, wherein the administered inhibitor comprises from about 0.01% to 5% by weight of said at least one lipoxygenase inhibitor.

17. The method as defined by claim 16, wherein said administered inhibitor composition comprises from 0.1% to 1% by weight of said at least one lipoxygenase inhibitor.

18. The method as defined by claim 17, wherein said administered inhibitor composition comprises from 0.1% to 0.8% by weight of said at least one lipoxygenase inhibitor.

19. The method as defined by claim 16, wherein the administered inhibitor containing composition comprises from 0.001% to 5% by weight of said at least one cyclooxygenase inhibitor.

20. The method as defined by claim 18, wherein the administered inhibitor containing composition comprises from 0.01% to 0.1% by weight of said at least one cyclooxygenase inhibitor.

21. The method as defined by claim 1, wherein the administered inhibitor containing composition is in the form of a lotion, a shampoo, tablets or a syrup.

* * * * *